US008419718B2

(12) United States Patent
Hunter

(10) Patent No.: US 8,419,718 B2
(45) Date of Patent: Apr. 16, 2013

(54) LASER HANDLE AND FIBER GUARD

(75) Inventor: Lowell D. Hunter, Los Gatos, CA (US)

(73) Assignee: AMS Research Corporation, Minnetonka, MN (US)

( * ) Notice: Subject to any disclaimer, the term of this patent is extended or adjusted under 35 U.S.C. 154(b) by 1371 days.

(21) Appl. No.: 12/120,866

(22) Filed: May 15, 2008

(65) Prior Publication Data

US 2008/0287934 A1    Nov. 20, 2008

Related U.S. Application Data

(60) Provisional application No. 60/938,074, filed on May 15, 2007.

(51) Int. Cl.
*A61B 18/20* (2006.01)
(52) U.S. Cl.
USPC .................................. 606/1; 128/898; 606/10
(58) Field of Classification Search .................. 606/1
See application file for complete search history.

(56) References Cited

U.S. PATENT DOCUMENTS

| 4,383,318 A | 5/1983 | Barry et al. |
| 4,402,569 A | 9/1983 | Bow et al. |
| 4,418,689 A | 12/1983 | Kanazawa |
| 4,646,737 A | 3/1987 | Hussein et al. |
| 4,648,892 A | 3/1987 | Kittrell et al. |
| 4,722,337 A | 2/1988 | Losch et al. |
| 4,760,840 A | 8/1988 | Fournier, Jr. et al. |
| 4,784,135 A | 11/1988 | Blum et al. |
| 4,802,461 A | 2/1989 | Cho et al. |
| 4,834,091 A | 5/1989 | Ott |
| 4,836,189 A | 6/1989 | Allred, III et al. |
| 4,862,886 A | 9/1989 | Clarke et al. |

(Continued)

FOREIGN PATENT DOCUMENTS

| WO | WO-9533518 | 12/1995 |
| WO | WO-9628998 | 9/1996 |

(Continued)

OTHER PUBLICATIONS

"Laserscope Accounces FDA Clearance for Pseudo-Follicolitis,"Laserscope.com/news/021401.htm, Feb. 14, 2001, pp. 1-2.

(Continued)

*Primary Examiner* — Henry M Johnson, III
(74) *Attorney, Agent, or Firm* — Kimberly K. Baxter; Gregory L. Koeller

(57) ABSTRACT

A protective handle for a mobile laser unit wherein the protective handle provides protection to a front section of the mobile laser unit from damage due to bumps and other impacts as the mobile laser unit is transported between treatment locations. The protective handle simultaneously acts to protect an attached optical fiber from damage during transport by limiting a bend radius of the laser fiber. The protective handle includes a U-shaped central segment having rear and forward surfaces defining a fiber optic support structure. The protective handle is attached to the mobile laser unit such that an optical fiber connector is centered within the U-shaped central segment and the optical fiber can rest on the fiber optic support structure.

10 Claims, 4 Drawing Sheets

U.S. PATENT DOCUMENTS

| | | |
|---|---|---|
| 4,907,235 A | 3/1990 | Kuizenga |
| 4,944,738 A | 7/1990 | Rodriguez |
| 4,981,138 A | 1/1991 | Deckelbaum et al. |
| 5,025,446 A | 6/1991 | Kuizenga |
| 5,066,291 A | 11/1991 | Stewart |
| 5,071,422 A | 12/1991 | Watson et al. |
| 5,147,353 A | 9/1992 | Everett |
| 5,151,909 A | 9/1992 | Davenport et al. |
| 5,231,641 A | 7/1993 | Ortiz |
| 5,242,390 A | 9/1993 | Goldrath |
| 5,242,437 A | 9/1993 | Everett et al. |
| 5,243,615 A | 9/1993 | Ortiz et al. |
| 5,249,192 A | 9/1993 | Kuizenga et al. |
| 5,257,991 A | 11/1993 | Fletcher et al. |
| 5,269,779 A | 12/1993 | Sogawa et al. |
| 5,300,061 A | 4/1994 | Easley et al. |
| 5,312,392 A | 5/1994 | Hofstetter et al. |
| 5,312,396 A | 5/1994 | Feld et al. |
| 5,409,481 A | 4/1995 | Poppas et al. |
| 5,409,483 A | 4/1995 | Campbell et al. |
| 5,421,323 A | 6/1995 | Herrmann et al. |
| 5,428,699 A | 6/1995 | Pon |
| 5,437,660 A | 8/1995 | Johnson et al. |
| 5,449,354 A | 9/1995 | Konwitz et al. |
| 5,451,221 A | 9/1995 | Cho et al. |
| 5,487,740 A | 1/1996 | Sulek et al. |
| 5,495,541 A | 2/1996 | Murray et al. |
| 5,520,679 A | 5/1996 | Lin |
| 5,542,944 A | 8/1996 | Bhatta |
| 5,593,404 A | 1/1997 | Costello et al. |
| 5,599,349 A | 2/1997 | D'Amelio |
| 5,607,420 A | 3/1997 | Schuman |
| 5,628,744 A | 5/1997 | Coleman et al. |
| 5,632,739 A | 5/1997 | Anderson et al. |
| 5,649,924 A | 7/1997 | Everett et al. |
| 5,662,646 A | 9/1997 | Fumich |
| 5,700,260 A | 12/1997 | Cho et al. |
| 5,733,279 A | 3/1998 | Konwitz et al. |
| 5,746,760 A | 5/1998 | Humphrey, Jr. |
| 5,772,658 A | 6/1998 | Konwitz |
| 5,776,127 A | 7/1998 | Anderson et al. |
| 5,776,175 A | 7/1998 | Eckhouse et al. |
| 5,778,395 A | 7/1998 | Whiting et al. |
| 5,798,518 A | 8/1998 | Coleman et al. |
| 5,807,389 A | 9/1998 | Gardetto et al. |
| 5,841,800 A | 11/1998 | Davenport et al. |
| 5,843,026 A | 12/1998 | Edwards et al. |
| 6,024,751 A | 2/2000 | Lovato et al. |
| 6,033,400 A | 3/2000 | Grossi et al. |
| 6,064,914 A | 5/2000 | Trachtenberg |
| 6,086,580 A | 7/2000 | Mordon et al. |
| 6,112,747 A | 9/2000 | Jones et al. |
| 6,156,030 A | 12/2000 | Neev |
| 6,197,025 B1 | 3/2001 | Grossi et al. |
| 6,379,347 B1 | 4/2002 | Maki et al. |
| 6,388,193 B2* | 5/2002 | Maynard et al. .......... 174/59 |
| 6,389,313 B1 | 5/2002 | Marchitto et al. |
| 6,423,055 B1 | 7/2002 | Farr et al. |
| 6,445,865 B1* | 9/2002 | Janus et al. .......... 385/135 |
| 6,482,199 B1 | 11/2002 | Neev |
| 6,510,274 B1* | 1/2003 | Wu et al. .......... 385/137 |
| 6,530,921 B1 | 3/2003 | Maki et al. |
| 6,554,824 B2* | 4/2003 | Davenport et al. .......... 606/3 |
| 6,554,825 B1 | 4/2003 | Murray et al. |
| 6,596,017 B1 | 7/2003 | Bolmsjo et al. |
| 6,678,455 B1* | 1/2004 | Knight .......... 385/134 |
| 6,699,239 B1 | 3/2004 | Stiller et al. |
| 2001/0032728 A1* | 10/2001 | Etemad-Moghadam ... 174/65 G |
| 2002/0193850 A1 | 12/2002 | Selman |
| 2004/0240825 A1* | 12/2004 | Daoud et al. .......... 385/135 |
| 2006/0275010 A1* | 12/2006 | Forrester .......... 385/136 |
| 2008/0287940 A1 | 11/2008 | Hunter |

FOREIGN PATENT DOCUMENTS

| | | |
|---|---|---|
| WO | WO-9710768 | 3/1997 |
| WO | WO-9715226 | 5/1997 |
| WO | WO-9832381 | 7/1998 |

OTHER PUBLICATIONS

"Laserscope Announces Approvable Letter Received for PDT Laser System for the Treatment of Head and Neck Cancer," Laserscope. com/news/052200.htm, May 22, 2000, pp. 102.

"Laserscope Announces High Power System: Lyra XP, AAD to be Introduced at the ADD," Laserscope.com/news/030800.htm, Mar. 8, 2000, pp. 1-2.

"Laserscope Announces PMA Application to U.S. Food and Drug Administration for PDT Treatment of Head and Neck Cancer," Laerscope.com/news/110999.htm, Nov. 9, 1999, pp. 1-2.

"Laserscope Receives FDA Clearnace or Market New Lyra Laser System for Hair Removal: First Laser Designed for Full Range . . . ," Laserscope.com/new/031300.htm, Mar. 13, 2000.

"Laserscope Reports First Quarter 2000 Results," Laserscope.com/news/050400.htm, May 4, 2000, pp. 103.

"Laserscope Report Fourth Quarter and Year End 2000 Results," Laserscope.com/news/021301.htm, Feb. 13, 2001, pp. 1-3.

"Laserscope Reports Increased Profits in Third Quarter 2000 Results," Laserscope.com/news/101900.htm, Oct. 19, 2000, pp. 1-3.

"Laserscope Signs Exclusive: Agreement with McKessinHBOC Medical Group for National Distribution of Aesthetic Laser Systems," Laserscope.com/news/121400.htm, Dec. 14, 2000.

"Researchers Report Decidedly Positive Two-Year Results Using Laserscope's Ultra High Power Laser and Dispoasable . . . " Laserscope.com/news/100300.htm, Sep. 29, 2000, p. 1.

Buttram, Veasay C., et al., "Indications for Myomectomy," Seminars in Reproductive Endocrinology 10(4) (Nov. 1992) 378-384.

Cecchetti. W., et al., "980 nm diode laser and fiber optic resectoscope in endourological surgery," Laser Applications in Medicine and Dent, Sep. 7-10, 1996. SPIE vol. 2922.

Conford, P.A., et al., "Transurethral Incision of the Prostate Using the Holmium: YAG Laser: a Catheterless Procedure," The Journal of Urology, vol. 159, Apr. 1998, pp. 1229-1231.

Dixon, J.A., "Argon and Neodymium YAG Laser Therapy of Dark Nodular Port Wine Stains in Older Patients," Lasers in Surgery and Medicine 6:5-11 (1986).

Gilling, P.J. et al., "Holmium Laser Enucleation of the Prostate (HoLEP) Combined with transurethral . . . " J. Endourol. 12:5 1998 457-459.

Gilling, P.J. et al., "Holmium laser prostatectomy: a technique in evolution" Curr. Opin. Urol. 1998, 8:11-15.

Gilling, P.J. et al., "The Use of the Holmium Laser in the Treatment of Benign Prostatic Hyperplasia" J. Endourol. 10:5 Oct. 1996 459-461.

Gilling, P.J. et al., "Combination Holmium and Nd:YAG Laser Ablation of the Prostate: Initial Clinical Experience," Journal of Enourology, vol. 9, No. 2, Apr. 1995, Mary Ann.

Gilling, P.J. et al., "Holmium Laser Resection of the Prostate Versus Neodymium: . . . "Urology, vol. 51, No. 2. 1999.

Gilling, P.J. et al., "Holmium Laser Versus Transurethral Resection of the Prostate: a Randomized Prospective Trial with 1-Year Followup," J Urol, vol. 162, Nov. 1999 1640-44.

Gilling. P.J. et al., "Holmium Laser Resection of the Prostate: Preliminary Results . . . " Urol 47:(1) 1996 48-51.

Grabo, Theresa N., et al., "Uterine Myomas: Treatment Options," JOGNN 28(1) (Jan./Feb. 1999), 23-31.

Guazzieri. S., et al., "The use of Ceralas D50 in Endourology—A Preliminary Report", XIIth Congress of the European Assoc. of Urol. Sep. 1-4, 1996 3 pgs.

In re Sarett, No. 7051, United States Court of Customs and Patent Appeals, 51 C.C.P.A. 1180; 327 F.2d 1005; 1964 CCPA LEXIS 475: 140U.S.P.Q. (BNA) 474.

In re Virgil W. Vogel and Paul W. Vogel, No. 8198, United States Court of Customs and Patent Appeals, 57 C.C.P.A,. 920; 422 F.2d 438;1970 CCPA LEXIS 423;164 U.S.P.Q. BNA 619.

Indman, Paul D., "High-Power Nd: YAG Laser Ablation of the Endometrium," J. Repro Med 36(7) (Jul. 1991), 501-504.

Indman, Paul D., "Hysteroscopic Treatment of Menorrhagia Associated with Uterine Leiomyomas," Obstetrics and Gynecology 81(5) part 1 (May 1993), 716-720.

Indman, Paul D., et al., "Uterine Surface Temperature Changes Caused by Endometrial Treatment with the Nd:YAG Laser," J Reprod Med 36 (7) (Jul. 1991), 505-512.

Kollmorgen, Thomas A., et al., "Laser Prostatectomy: Two and a Half Years' Experience with Aggressive Multifocal Therapy," Urology, 48(2) 1996 217-222.

Kuntzman, Randall S., et al., "High-Power (60-Watt) Potassium-Titanyl-Phosphate Laser Vaporiztion Prostatectomy . . . ," Urology, 49(5), pp. 703-708, Elsevier Science, Inc. 1997.

Kuntzman, Randall S., et al., "Potassium-Titanyl-Phosphate Laser Vaporization of the Prostate: A Comparative Functional and Pathologic Study in Canines," Urology 48(4) 1996.

Lahaye, C.T.W., et al., "Optimal Lasre Parameters for Port Wine Stain Therapy: A Theoretical Approach," Phys. Med. Biol., vol. 30, No. 6, pp. 573-587, 1985.

Langhaler, M., M.D., et al., "Effects of Argon, Dye, and Nd:YAG Lasers on Epidermis, Dermis, and Venous Vessels," Lasers in Surgery and Medicine, vol. 6, pp. 87-93, 1986.

Le Duc, A., et al., "Holmium Laser Resection of the Prostate," Eur Urol 1999: 35: 155-160.

Malek, Reza S., et al., "High Power Potassium-Titanyl-Phosphate Laser Vaporization Prostatectomy," The Journal of Urology, vol. 163, Jun. 2000, pp. 1730-1733.

Malek. Reza S., et al., "High-Power Potassium-Titanyl-Phosphate (KTP/532) Laser Vaporization Prostatectomy: 24 Hours Later," Urology, 51(2) pp. 254-256, 1998.

Mansell et al., "Evaluating the effect of transmissive optic thermal lensing on laser beam quality with . . . ," Applied Optics, vol. 40, No. 3, Jan. 20, 2001, pp. 366-374.

Memorandum and Order Regarding Construction of Patent Claims, U.S. District Court for the District of Massachusetts, Civil Action No. 3:07, CV-30109-MAP, Jul. 31, 2008, 39 pg.

Morettii, Michael, "Laserscope's Lyra Laser Proves Multi-Functional," Aesthetic Buyers Guide, Medical Insight, Inc., Jul. 2000.

Mottet, Nicolas, M.D., PH.D., et al., "Randomized Comparison of Transurethral Electroresection and Holmium: . . . " Journal of endourology, vol. 13, No. 2,Mar. 1999, pp. 127-130.

Kuntzman, Randall S., et al., "High-Power Potassium Titanyl Phosphate Laser Vaporization Prostatectomy," Mayo Clin Prac, 1998:798-801.

Narayan, P., et al., "Transurethral Evaporation of the Prostate for Treatment of Benign Prostatic Hyperplasia: Results," J Urol., vol. 157(4), Apr. 1997, 7 pages.

Reply to Counterclaims Civil Action No. 3:07-cv-30109-MAP (Aug. 10, 2007) *American Medical Systems, Inc. and Laserscope* v. *Biolitec, Inc.* 3 pages.

*Rosco, Inc.* v. *Mirror Lite Company*, United States Court of Appeals for the Federal Circuit, 01-1271, 1302 (2002).

Rosenfeld, Harold, et al., "Treatment of Cutaneous and Deep Vascular Lesions with the Nd:YAG Laser" Lasers in Surgery and Medicine, vol. 6, pp. 20-23, 1986.

Schnieder, Ellen Meyer, "Try Different Lasers for Treatng Blood Vessel Disorders," Cosmetic Surgery Times, Oct. 1999.

Svelto,Orazio "Principles of Lasers," Fourth Ed., pp. 480-482, Plenum Press, New York, NY, 1998.

Van Gemert, Martin J.C., PH.D., et al., "Treatment of Port-Wine Stains: Analysis" Medical Instrumentation, vol. 21, No. 4, pp. 213-217,1987.

Van Germet, Martin J.C., PH.D., et al., "Is There an Optimal Laser Treatment for Port Wine Stains?", Lsers in Surgery and Medicine, vol. 6, pp. 76-83, Alan R. Liss, Inc., 1986.

Van Swol, Christiaan F.P., et al., "Physical Evaluation of Laser Prostatectomy Devices," Lasers in Urology, vol. 2129, 1994.

Zelickson, Brian D., M.D., et al., "Preliminary Results of the Lyra Long Pulsed Nd . . . ," Abstract of the Presentation by Dr. Brian Zelickson at tthe ISCLS in May 2000.

* cited by examiner

LASER HANDLE AND FIBER GUARD

PRIORITY CLAIM

The present application claims priority to U.S. Provisional Application Ser. No. 60/938,074, filed May 15, 2007, and entitled, "LASER HANDLE AND FIBER GUARD", which is herein incorporated by reference in its entirety.

FIELD OF THE DISCLOSURE

This invention relates to the field of laser systems and optical fibers used for the treatment of soft tissue. More specifically, the present invention is directed to a handle for a laser system that facilitates movement of the laser system while protecting an attached optical fiber from damage.

BACKGROUND OF THE INVENTION

Medical lasers have been used in treatment procedures involving various practice areas including, for example, urology, neurology, otorhinolaryngology, general anesthetic ophthalmology, dentistry, gastroenterology, cardiology, gynecology, and thoracic and orthopedic procedures. Generally, these procedures require precisely controlled delivery laser energy, and often the area to which the energy is to be delivered is located deep within the body, for example, at the prostate or at the fallopian tubes. Due to the location of the target tissue deep within the body, the medical procedure generally requires use of a flexible and maneuverable optical fiber. Depending upon the requirements for a light source, a variety of light sources can be used in conjunction with the optical fiber including, for example, pulsed lasers, diode lasers, and neodymium lasers. Representative lasers used in medical treatment procedures include Ho:YAG lasers and Nd:YAG lasers.

Generally, a surgical probe is utilized in the treatment of body tissue with laser energy. The surgical probe generally comprises an optical fiber coupled to a laser source, wherein the probe is positioned so that a probe tip can be positioned adjacent targeted tissue. Laser energy is directed out of the probe tip of the optical fiber onto desired portions of the targeted tissue. The optical fiber coupled to the laser source is required to be somewhat flexible such that the optical fiber can be manipulated. However, the flexibility of the optical fiber can contribute somewhat to the possibility of damage to the optical fiber, should it get bumped or crushed.

The laser unit is frequently used in clinic or office setting where out-patient medical procedures may be performed. As such, the laser unit frequently comprises a mobile unit capable of being moved between treatment locations and is therefore subject to bumping and possible damage. The laser unit is generally is an expensive piece of capital equipment and any damage resulting from frequent movement of the laser unit is not only expensive to repair but can also result in the laser unit being left inoperative for some time. In addition, any laser downtime can affect the ability to perform previously scheduled procedures resulting in patient delay in obtaining the services they require. Further, the optical fiber that extends from the laser unit can also be damaged and require replacement, even if the laser unit itself is not damaged. Damage to the optical fiber also increases the cost of performing procedures due to the need to replace the optical fiber and potential delay in doing so. Hence, there remains a need for the laser unit and the optical fiber to be protected from damage that can result as the unit is used and moved about the treatment environment.

SUMMARY OF THE INVENTION

The present invention comprises a mobile laser unit having a protective handle providing protection to a front section of the mobile laser unit from damage due to bumps and other impacts as the mobile laser unit is transported between treatment locations. The protective handle simultaneously acts to protect an attached optical fiber from damage during transport by limiting a bend radius of the laser fiber. The protective handle includes a U-shaped central segment having rear and forward surfaces defining a fiber optic support structure. The protective handle is attached to the mobile laser unit such that an optical fiber connector is centered within the U-shaped central segment and the optical fiber can rest on the fiber optic support structure.

In another aspect, a method of protecting a mobile laser unit from damage during transport can comprise providing a protective handle having a U-shaped center segment with a fiber support structure defined between a rear curved surface and a front curved surface. The protective handle can be attached to the laser unit such that an optical fiber connector on the laer unit is centered within the U-shaped center segment. With the protective handle so attached, the protective handle extends forward of anything on the laser unit. An optical fiber can be attached to the optical fiber connector such that the optical fiber passes between side portions of the "U"-shaped center segment with the optical fiber resting on the fiber support structure so as to limit a bend radius of the optical fiber. The laser unit can be transported between treatment locations wherein the protective handle protects both a front surface of the laser unit and the optical fiber from damage during maneuvering.

Although specific examples have been illustrated and described herein, it will be appreciated by those of ordinary skill in the art that any arrangement calculated to achieve the same purpose could be substituted for the specific examples shown. For example, other configurations could be substituted for the example handle noted above.

BRIEF DESCRIPTION OF THE DRAWINGS

These as well as other objects and advantages of this invention will be more completely understood and appreciated by referring to the following more detailed description of the presently preferred exemplary embodiments of the invention in conjunction with the accompanying drawings, of which.

Figure 1:
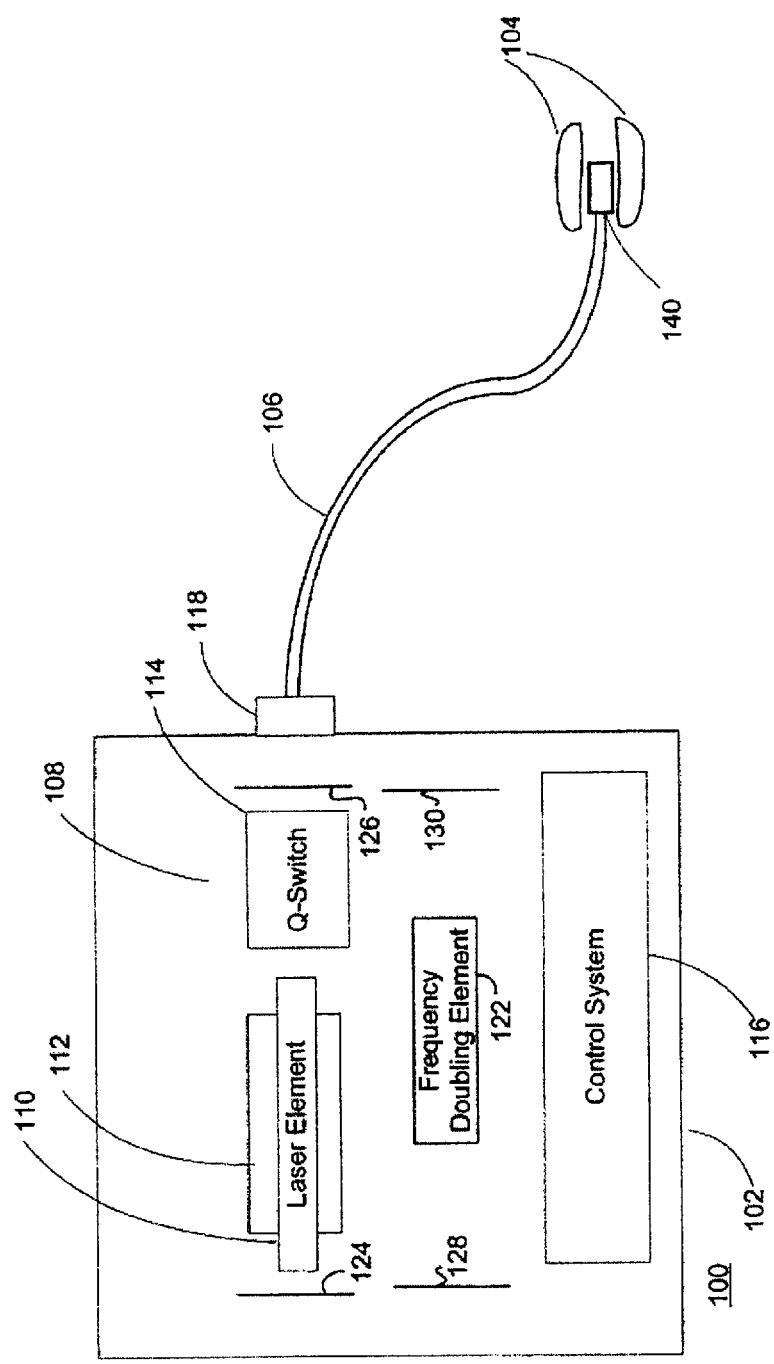
FIG. 1 is a schematic illustration of a representative laser system with an optical fiber attached thereto.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF EMBODIMENTS OF THE INVENTION

The present invention includes a mobile laser unit having a protective handle protecting a front section of the mobile laser unit from damage due to bumps and other impacts as the mobile laser unit is transported between treatment locations. The protective handle simultaneously acts to protect an attached optical fiber from damage during transport by limiting a bend radius of the laser fiber. The protective handle includes a U-shaped central segment having rear and forward surfaces defining a fiber optic support structure. The protective handle is attached to the mobile laser unit such that an optical fiber connector is centered within the U-shaped central segment and the optical fiber can rest on the fiber optic support structure. In one preferred embodiment, the protective handle is utilized with a Greenlight HPS system manufactured by American Medical Systems of Minnetonka, Minn. and as described in U.S. Pat. Nos. 6,554,824 and 6,986,764, which are herein incorporated by reference.

Referring to FIG. 1, there is depicted a block diagram showing an exemplary laser system 100 which may be employed for implementing the present invention. Laser system 100 includes a solid-state laser unit 102, which is used to generate laser light for delivery through optical fiber 106 to target tissue 104. Laser unit 102 is capable of being operated in a pulsed mode or continuous wave.

Laser unit 102 more specifically comprises a laser element assembly 110, pump source 112, and frequency doubling crystal 122. In the preferred-embodiment, laser element 110 outputs 1064 nm light which is focused into frequency doubling crystal 122 to create 532 nm light. According to one implementation, laser element assembly 110 may be neodymium doped YAG (Nd:YAG)crystal, which emits light having a wavelength of 1064 nm (infrared light) when excited by pump source 112. Laser element 110 may alternatively be fabricated from any suitable material wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthahum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc lamps, flashlamps, and laser diodes.

A Q-switch 114 disposed within laser unit 102 may be operated in a repetitive mode to cause a train of micropulses to be generated by laser unit 102. Typically the micropulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser unit 102 is provided with a control system 116 for controlling and operating laser unit 102. Control system 116 will typically include a control processor which receives input from user controls (including but not limited to a beam on/off control, a beam power control, and a pulse duration control) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce 532 nm light. The frequency doubled, shorter wavelength light is better absorbed by the hemoglobin and char tissue, and promotes more efficient tissue ablation. Finally, the green light leaves only a thin char layer with little pre and post operative bleeding.

Laser unit 102 further includes an output port 118 couplable to optical fiber 106. Output port 118 directs the light generated by laser unit 102 into optical fiber 106 for delivery to tissue 104. Mirrors 124, 126, 128, and 130 direct light from the lasing element 110 to the frequency doubling crystal 122, in addition to forming the resonant cavity of the laser. Mirrors 124, 126, 128, and 130 are configured for focusing the light to form an image just in front of the frequency doubling crystal 122 on the side closer to mirror 130, and to compensate for thermal lensing in the lasing element. Although mirrors 124, 126, 128, and 130 are illustrated as flat and parallel to the walls of the laser, typically the focusing is achieved by curving and/or angling the mirrors. Alternatively transmissive optical elements could be used to focus the light and compensate for the thermal imaging. Mirrors 124, 128 and 130 reflect both the wavelength of light produced by the lasing element (e.g. 1064 nm) and the wavelength of the frequency doubled light (e.g. 532 nm). Mirror 126 only reflects the light originating from the lasing element 110 (e.g. 1064 nm) but is transparent to the frequency doubled light (e.g. 532 nm), forming an output window. Higher harmonic outputs may also be generated from the 1064 nm line, or other line amplified in the laser, including third and fourth harmonics, for shorter wavelengths. Other laser systems may be used, including but not limited to Sapphire lasers, diode lasers, and dye lasers, which are adapted to provide the output power and wavelengths described herein, including wavelengths in the ranges from 200 nm to 1000 nm and from 1100 nm to 1800 nm, for example.

While a bare fiber may be utilized for certain procedures, optical fiber 106 preferably terminates in a tip 140 having optical elements for shaping and/or orienting the beam emitted by optical fiber 106 so as to optimize the tissue ablation process, for example a side-firing fiber. Output port 118 directs the light generated by laser unit 102 into optical fiber 106 for delivery to tissue 104. At times it is necessary to physically move the laser unit 100 between different treatment locations Regardless if a neodymium doped solid-state laser is used, or a Q-switched solid-state laser is used, each requires the use of optical fiber 106 to deliver the laser light used in carrying out the specific procedure to be accomplished. At times of use, the optical fiber 106 is maneuvered into an extended position. The optical fiber 106 extends from the laser unit 102 through a fiber connector 170 shown in FIGS. 3 and 4 and is manipulated into position to accomplish a required task. The task may include, for example, insertion through a bodily incision or orifice to ablate particular tissue. The laser unit 102 includes a handle 152 allowing a user to move the laser unit from location to location or during a treatment procedure with the optical fiber 106 to facilitate proper positioning of the optical fiber 106.

The handle 152 of the present invention is designed and structured such that the handle 152 incorporates the function of not only facilitating transport of the laser unit 102 but simultaneously action as an optical fiber guard. The handle 152 is formed such that a user can either push or pull the laser unit 102 during relocation and/or repositioning. The handle 152 includes a U-shaped center segment 154 that accommodates the optical fiber 106. The "U"-shaped center segment 154 comprises a number of contours and radii to minimize a bend radius and correspondingly minimize stress applied to the optical fiber 106 should the optical fiber 106 be forced to conform to the shape of the handle 152 during accidental contact. Further, the handle 152 is positioned slightly forward of a front cover 156 on the laser unit 102. With the handle 152 positioned forward of the front cover 156, the handle 152 makes contact with walls or other obstructions before the front cover 156, thus preventing damage to the front cover 156 and the laser unit 102 itself.

Figure 2:
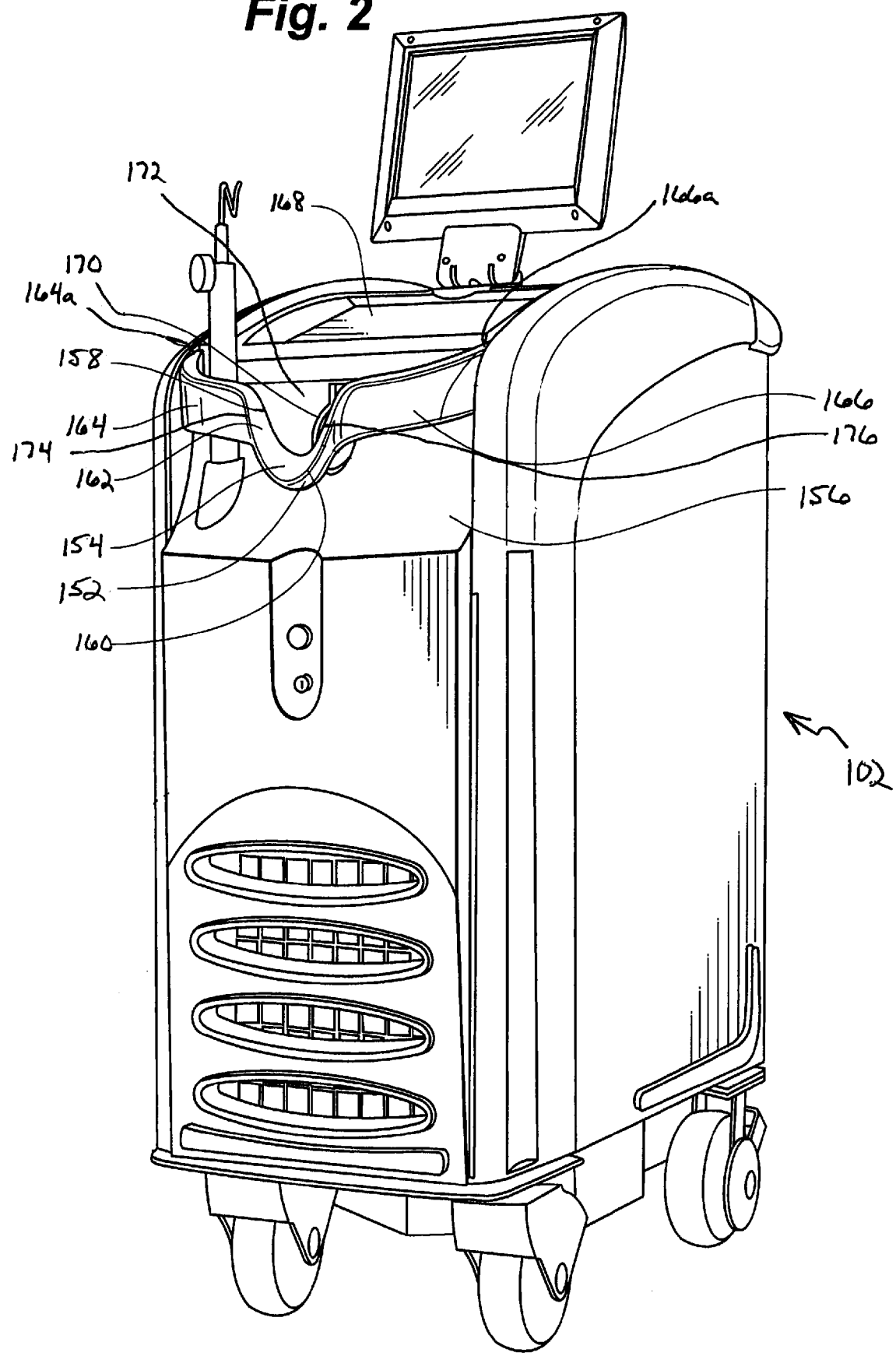
FIG. 2 is a front, perspective view of a mobile laser unit having a protective handle according to an embodiment of the present invention.
Figure 3:
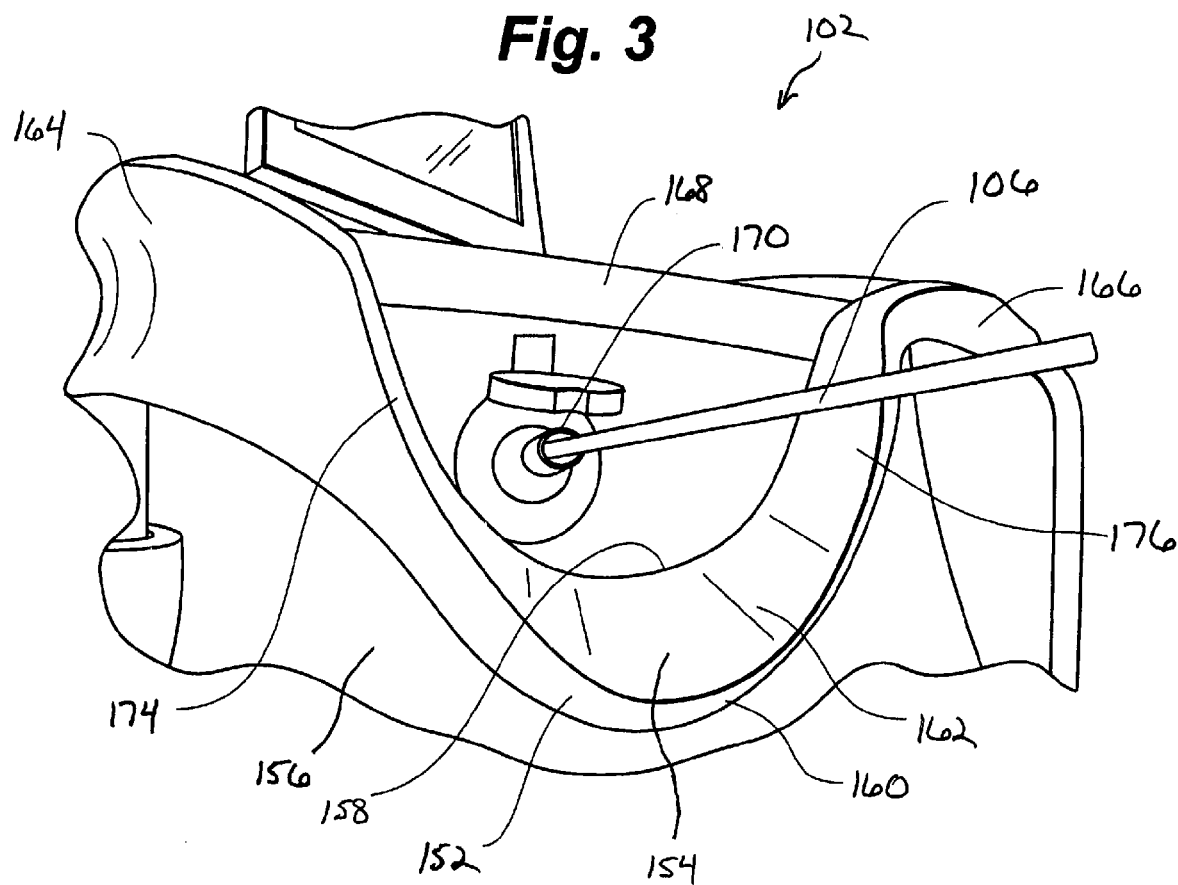
FIG. 3 is a front, perspective view of the protective handle of FIG. 2.
Figure 4:
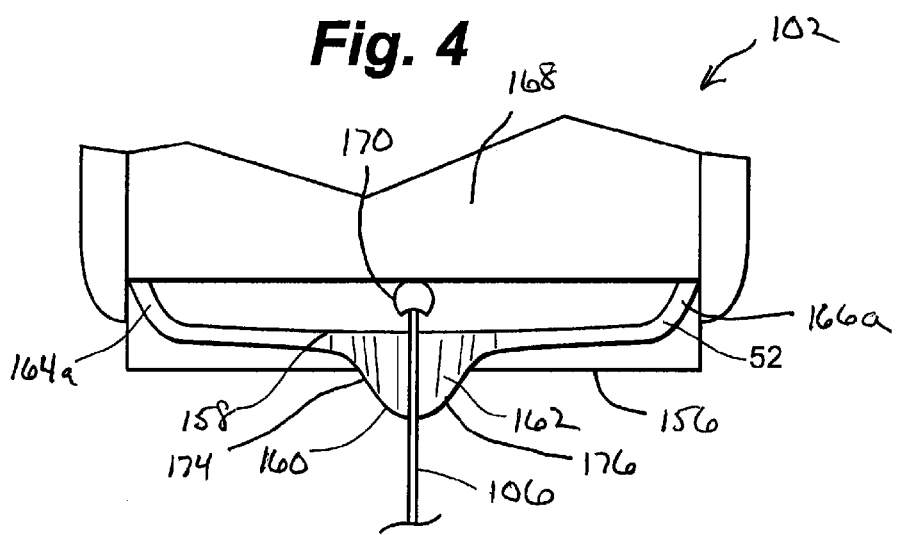
FIG. 4 is a plan view of the protective handle of FIG. 2.

Referring to FIGS. 2, 3 and 4, handle 152 generally comprises U-shaped center segment 154 defined between a rear curved surface 158 and a front curved surface 160. The rear curved surface 158 is positioned higher than the front curved surface 160 to define a fiber support structure 162. The fiber support structure 162 prevents kinks from forming in the optical fiber 106 and prevents the optical fiber 106 from bending precipitously and thereby damaging the optical fiber 106. U-shaped center segment 154 terminates in two shoulders 164, 166. Distal ends 164a, 166a of each shoulder 164, 166 affix the handle 152 to the laser unit 102, on either side of a top surface 168 of the laser unit 102. As shown in FIGS. 2, 3 and 4, handle 152 can comprise a single, integrally molded piece that includes the two shoulders 164, 166 as well as the U-shaped center segment 154. Alternatively, the handle 152 can comprise multi-piece construction with the shoulders 164, 166 and U-shaped center segment 154 affixed together.

As shown in FIGS. 3 and 4, an optical fiber connector 170 is positioned on a front surface 172 of the laser unit 102. Generally, optical fiber connector 170 is centered with respect to the U-shaped center segment 154. Thus, the optical fiber 106 passes between side portions 174, 176 of the "U"-shaped center segment 154 when the optical fiber 106 is operably attached to the fiber connector 170. As shown in FIG. 3, the rear curved surface 158 is defined by a smaller radius than a radius of the front curved surface 160 with the fiber support structure 162 sloping forward from the rear curved surface 158 to the front curved surface 160. The gently sloping fiber support structure 162 provides a surface on which the optical fiber 106 can rest. The fiber support structure 162 limits a bend radius of the optical fiber 106 such that sharp bends or kinks cannot form in the optical fiber 106 that can lead to transmission and/or signal losses in the optical fiber 106. Further, the handle 152 is constructed of radiused edges such that there are no sharp edges that can cut, nick or otherwise damage the optical fiber 106.

Figure 5:
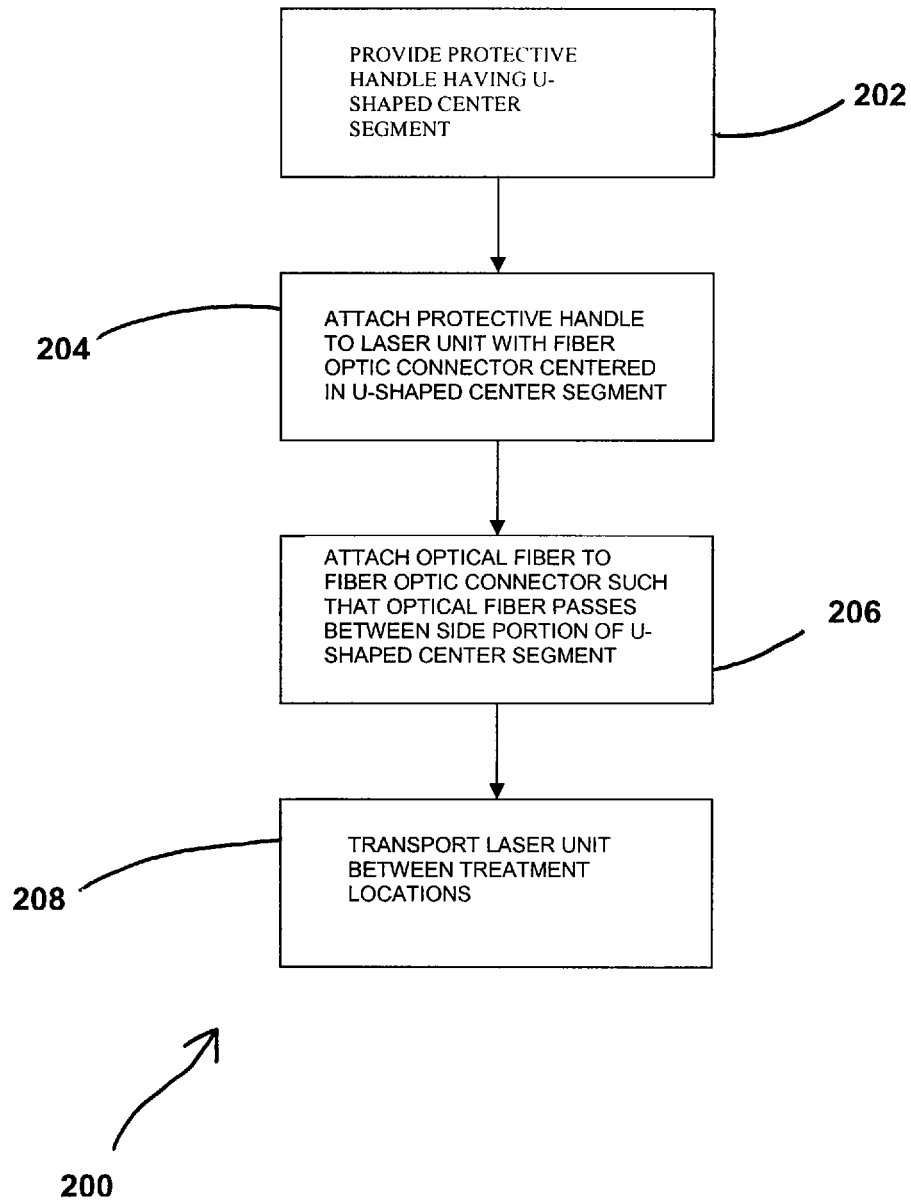
FIG. 5 is a flow chart illustrating a method of protecting a laser unit and optical fiber with a protective handle according to an embodiment of the present invention.

A representative method 200 of the present invention is illustrated schematically in FIG. 5. In a first step 202, handle 152 can be provided including U-shaped center segment 154 with fiber support structure 162 defined between the rear curved surface 158 and the front curved surface 160. In a second step 204, the handle 154 can be attached to the laser unit 102 such that the optical fiber connector 170 is centered within the U-shaped center segment 154. With the handle 154 attached to the front surface 172 of the laser unit 102, the handle 154 projects forward of anything on the laser unit 102. In a third step 206, the optical fiber 106 can be attached to the optical fiber connector 170 such that the optical fiber 106 passes between side portions 174, 176 of the "U"-shaped center segment 154. The optical fiber 106 resides on the gently sloping fiber support structure 162, which limits a bend radius of the optical fiber 106 such that sharp bends or kinks cannot form in the optical fiber 106. In a fourth step 208, the laser unit 102 can be transported between treatment locations wherein the handle 152 protects both the front surface 172 and the optical fiber 106 from damage during maneuvering.

The shape of the handle 152 provides for a comfortable, ergonomic contour when grasping the handle 152 to move the laser unit 102 between treatment locations. Further, the shape of the handle 152 dispenses with the need for a separate guard for the optical fiber 106 as the handle 152 also acts as a fiber guard, protecting the optical fiber 106 from bumps and impacts. Positioning of the handle 152 on the laser unit 102 also provides for protection of the front surface 172 of the laser unit 102 because the handle 152 absorbs any impacts instead of the front surface 172 absorbing the impacts and possibly causing damage to the laser unit 102.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents.

The invention claimed is:

1. A medical laser system comprising:
   a laser unit having a front section, the front section including a fiber optic connector;
   a protective handle having a "U"-shaped center segment comprising a rear curved surface and a front curved surface defining a fiber support surface that slopes downwardly from the rear curved surface to the front curved surface, wherein the rear curved surface is attached to the front section; and
   an optical fiber operably connected to the fiber optic connect wherein the optical fiber is supported on the fiber support surface,
   wherein the front curved surface projects forward of the front section to simultaneously protect the front section and the optical fiber from damage during transport of the laser unit.

2. The medical laser system of claim 1, wherein the "U"-shaped center segment further comprises a first side portion and a second side portion.

3. The medical laser system of claim 2, wherein the rear curved surface defines a rear radius smaller than a front radius defined by the front curved surface.

4. The medical laser system of claim 1, wherein the "U"-shaped center segment further comprises two shoulder segments wherein each shoulder segment comprises a distal end attached to the laser unit.

5. The medical laser system of claim 1, wherein the protective handle comprises a single molded piece.

6. The medical laser system of claim 1, wherein the protective handle comprises multiple pieces affixed together to form the protective handle.

7. A method of protecting a mobile laser unit from damage during transport comprising:
   providing a protective handle having a U-shaped center segment with a downwardly sloping fiber support structure defined between a rear curved surface and a front curved surface;
   attaching the rear curved surface to a front surface of a mobile laser unit such that an optical fiber connector on the front surface is centered within the U-shaped center segment and the front curved surface extends forward of the front surface; and coupling an optical fiber to the optical fiber connector such that the optical fiber passes between a pair of side portions on the protective handle.

8. The method of claim 7, further comprising:

moving the laser unit between treatment locations wherein the forward position of the front curved surface on the protective handle protects both the front surface and the optical fiber from damage during maneuvering.

9. The method of claim 7, further comprising:

limiting a bend radius of the optical fiber by proving a pair of side portions on opposed sides of the fiber support structure.

10. The method of claim 7, further comprising:

forming the protective handle to have radiused surfaces.

* * * * *